US005174280A

United States Patent [19]

Gruenwald et al.

[11] Patent Number: 5,174,280

[45] Date of Patent: Dec. 29, 1992

[54] SHOCKWAVE SOURCE

[75] Inventors: Michael Gruenwald, Germering; Harald Eizenhoefer, Munich, both of Fed. Rep. of Germany

[73] Assignee: Dornier Medizintechnik GmbH, Germering, Fed. Rep. of Germany

[21] Appl. No.: 491,315

[22] Filed: Mar. 9, 1990

[30] Foreign Application Priority Data

Mar. 9, 1989 [DE] Fed. Rep. of Germany ....... 3907605

[51] Int. Cl.$^5$ .............................................. A61B 17/22

[52] U.S. Cl. ................................ 128/24 EL; 367/175

[58] Field of Search ........................ 128/24 A, 24 EL; 606/127, 128; 181/106, 118, 120; 367/147, 151, 175

[56] References Cited

U.S. PATENT DOCUMENTS

| | | | |
|---|---|---|---|
| 3,451,260 | 6/1969 | Thurstone | 367/151 |
| 3,755,698 | 8/1973 | Trott | 367/151 |
| 3,895,188 | 7/1975 | Ingraham | 367/151 |
| 4,241,432 | 12/1980 | Barber et al. | 367/151 |
| 4,528,853 | 7/1985 | Lerch et al. | 367/151 |
| 4,697,579 | 10/1987 | Wessels et al. | 128/24 EL |
| 4,893,614 | 1/1990 | Takayama et al. | 128/24 EL |
| 4,924,858 | 5/1990 | Katona | 128/24 EL |

FOREIGN PATENT DOCUMENTS

| | | | |
|---|---|---|---|
| 3505855 | 2/1985 | Fed. Rep. of Germany | 128/24 EL |
| 1393489 | 5/1988 | U.S.S.R. | |
| 1405885 | 6/1988 | U.S.S.R. | |

OTHER PUBLICATIONS

Reitz et al., "Two Parabolic Reflector Underwater Transducers", The Journal of the Acoustical Society of America, vol. 19, No. 1, Jan. 1947, pp. 35–42.

*Primary Examiner*—Lee S. Cohen
*Assistant Examiner*—K. M. Pfaffle
*Attorney, Agent, or Firm*—R. H. Siegemund

[57] ABSTRACT

A shockwave source and generating device includes a ring shaped or cylindrical wave generator having a central axis for radiating shockwaves in an axial direction or radially towards a parabolic reflector so that any yet unreflected radiation from the generator is intercepted by the reflector and reflected towards a focal point on that axis.

9 Claims, 3 Drawing Sheets

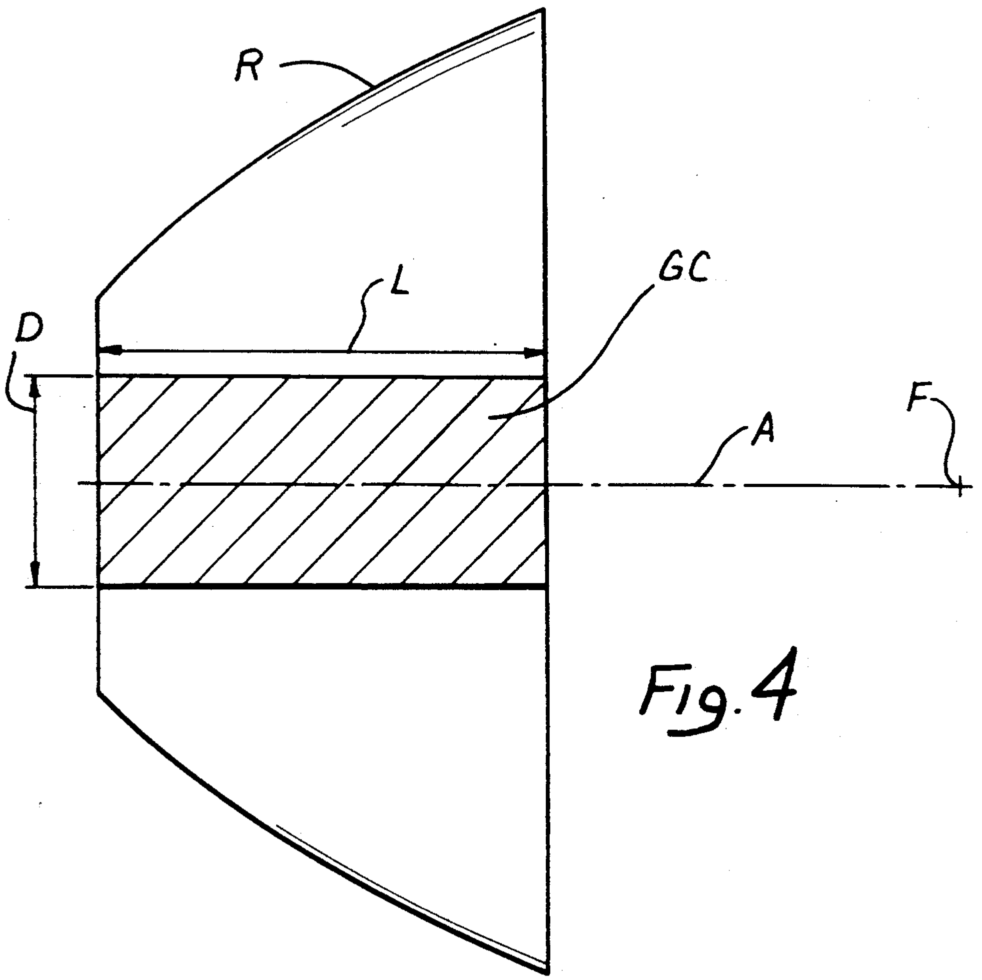
Fig. 4
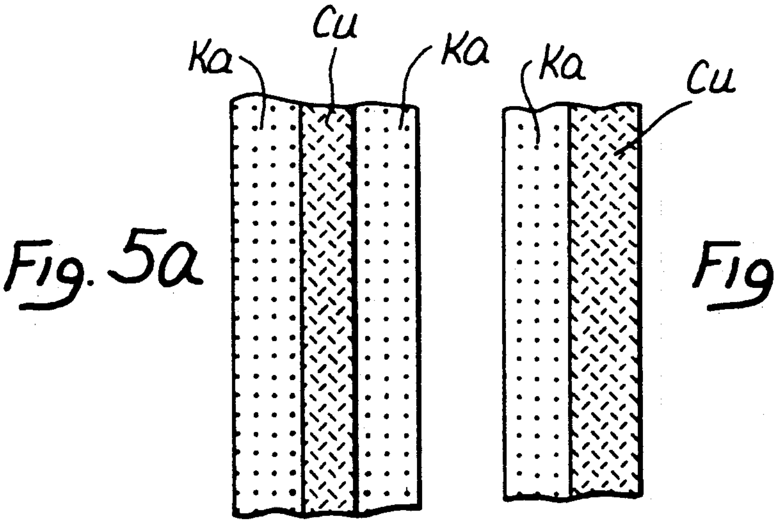
Fig. 5a
Fig. 5b
Fig. 6a
Fig. 6b

SHOCKWAVE SOURCE

BACKGROUND OF THE INVENTION

The present invention relates to a shockwave source for use in and as a part of a lithotripter and includes an areal wave generator cooperating with a parabolic reflector.

U.S. Pat. No. 3,942,531 and others, e.g. 4,539,989; 4,570,634; 4,622,969; 4,662,375; 4,809,682 show pointlike sources for the generation of shockwaves in a lithotripter. Contrary to the technology which is included in the reference and others an areal shockwave source is shown in German printed patent application 31 19 295. The source as disclosed here is composed of a plurality of individual piezoceramic elements. They are arranged e.g. in a self focusing configuration i.e. they delineate as spherical calotte or they are arranged to cooperate with a reflector or a lens in order to obtain focusing of the areally produced shockwaves. The shockwave front can be produced through appropriate control which is feasible on account of the nonlinear propagation of a single sound wave provided, the intensity is sufficiently high.

German printed patent application 34 47 440 suggests a shockwave generator for the contactfree non-invasive lithotripsy which includes an areal wave generator which in this case is constructed as an electromagnetic shockwave pipe and cooperating with a parabolically shaped reflector. This reflector focuses the shockwave as it is produced in a planar configuration originally into the concrement to be comminuted in the body of a patient. Such kind of source is basically in the background of the invention alluded to above and which will be improved by detailed features of the invention.

In order to comminute concrements very efficiently in situ and in vivo with as few side and after effects of the treatment as possible, one can summarize the following essential technical requirements for the formation of a shockwave system. First of all the dynamics of the power is to have is to be very high; the device must provide for good focusing of, preferably, unipolar pulses with low pressure and particularly low tension produced as the wave reaches the body of the patient. It is necessary to locate on one hand the concrements through ultrasonic and/or X-rays with sufficient accuracy and to place the focus of the lithotripter into that location. A long use life is desirable and owing to the fact that often only very limited space is available in the immediate vicinity of the patient, the device should be of a compact construction.

In some form or another these demands are satisfied individually, but often not completely and as far as known to us they are not all satisfied in one piece of equipment, e.g. the pointlike source for shockwave energies as they are widely used in commercial application for kidney stone comminution, does provide a high power but the dynamic range is only limited to lower power levels. Moreover it was found that occasionally a supplemental, centrally (axially) positioned ultrasonic locating device may interfere with the comminuting device and vice versa.

Self focusing piezosystems are very large owing to the low local intensity in ultrasonic production. Planar electromagnetic coil systems do have adequate powder density in the source but it is difficult to obtain high aperture configuration for focusing with a lens system. Self focusing electromagnetic calotte system have unfortunately a very limited use life.

DESCRIPTION OF THE INVENTION

It is an object of the present invention to provide a new and improved shockwave source and generation for lithotripsy which optimizes as much as possible satisfying the demands outlined above.

It is a particular object of the present invention to provide a new and improved shockwave source and generator for contactfree lithotripsy using an areal wave generator as well as with a parabolic reflector.

In accordance with the preferred embodiment of the present invention it is suggested to provide an annular i.e. ring shaped or cylindrical shockwave generator facing the reflector which through single reflection reflects shockwaves as produced in a wavefront by the annular generator, into a focal point situated on the longitudinal axis that is common to the reflector and the annual generator. The annulus may be a ring that provides an areal shockwave by an axial face so that the waves are parallel to that common axis towards the parabolic reflection or the annulus maybe a cylinder whose outer cylindrical face provides radial outward propagating shockwaves towards parabolic reflection.

This kind of a device does indeed satisfy the requirement of adequate power dynamics and is a device with a high aperture and does in fact permit integration with a locating system. Very importantly the property of a parabolic or better, paraboloidic surface is used in order to concentrate and focus a planar wavefront to a single focal point with as high efficiency as possible.

It can thus be seen that basically the annular configuration of the source is situated to face the entrance plane of the parabolic reflector. If the annulus is a ring then owing to the finite thickness a kind of aperture cylinder is established by the aperture. The center of course is necessary in order to permit for example locating the focus "through" the central opening of the cylinder or annulus. The opening should of course be open in axial direction and that is the reason for having an annular ring of the source in the first place. For a particular minimal aperture angle the boundary conditions are such that that portion of the ultrasonic waves that is reflected by the upper edge of the parabole, should still reach the focal point. This means that there are minimal aperture dimension since otherwise that part of the radiation produced would be lost and would be intercepted again by the ring if the aperture is made smaller (self shading). A larger radius or diameter inherently would reduce the power output in the first place. The reflected and now converging wavefront is as stated focused by operation of a high aperture condition into or through the central free area but only the operation of the outer parabolic zone so that the central portion thereof is available for a locating device.

The arrangement's design can be variable of focusing. This is particularly so if the ring establishing has such a large inner diameter that it can be looped around the patient. In that case the focus does not have to be on the other side of the ring i.e. opposite the focusing reflector. The limiting factor in this case is not the shading effect of the source itself but the particular configuration of the patient and the physical location of that part of the body that is to be treated with shockwaves. This is a matter of finding the proper space and location of the concrement in the body of the patient in the space delineated in general to the annulus of the source. In another configuration the focus is behind the source and in this case then the shockwaves run through the aperture and the shading effect mentioned above will take place.

The particular source geometry has the following advantages. First of all there is a high degree of flexibility concerning the size and dimension of the source so that a planar areal source can be configured, designed and constructed in order to optimize the requirements of power and variations thereof. The arrangement as such can be practiced either with piezoelectric devices or with electromagnetic ultrasonic pulse production. The planar configuration of the source is such and makes simple isolation and contacting as far as high power design is concerned. The focusing is excellent owing to high aperture conditions and owing to the fact that the central part is free from shockwaves that are being produced and have not yet been reflected. The central, unoccupied zone permits placing of an ultrasonic locating system and/or an X-ray system. The situation is such that the locating procedure and the treatment will not interfere. The reduction of axial compression on one hand and the tension component in the focusing shockwave field is reduced owing to the fact that centrally no shockwave is being produced.

As an alternative configuration a cylindrical arrangement is proposed which does not radiate in a plane that is at right angle to the axis but radiates from the cylindrical surface itself. The radiation is directed toward the surrounding reflector. The reflector can be deemed to be produced geometrically by rotating a partial parabola around a particular line which runs through the center of the focal point of the parabola and thus establishes itself as the axis of symmetry which in turn has to coincide with the axis of the cylindrical shockwave source. The device can be realized by a compact tube made of a piezoceramic material upon which a piezoceramic element is placed along the outer periphery. This geometry permits a high variability concerning focal length and aperture size which is quite analogous to the design of an ellipsoidal reflector in a water submerged arc discharge. This feature is important if the source is possessed of a high power density.

In lieu of the foregoing compact piezoceramic design and in the case for a demand of large powers, one could use an electromagnetic source having a cylindrical geometry. A longitudinally, axially extending coil cooperates with a conductive cylindrical jacket which is used as the radiating membrane. The ultrasonic source in this case is thus comprised of a coil, an electrical insulation and an electrically conductive outer cylinder. As the coil is energized with current pulses repelling obtains as between the coil in which the primary current flows and the membrane in which a secondary current is induced. The deflection of the membrane is in this case, a radial one and one obtains a radial shockwave field. Technical problems suggested by a compactness of space, and the requirement of accurate coupling between coil membrane and insulation as well as the extension in the peripheral direction pursuant to is radial expansion are all solvable by those skilled in the art. Among still other problems there is a total amount of surface available and necessary for a given energy intensity, which can be obtained under observation of a minimal radius.

In a particular configuration a single layer cylindrical coil is used which is wound and established through flat conductors. They are arranged on an electrical insulator. The cylindrical membrane may be comprised of a copper layer coated with a stainless steel layer. Cooper provides for good electrical properties necessary for induction while the stainless steel jacket establishes the strength conditions of the membrane. However this is not that essential. The cylindrical membrane could be provided through a laminated multilayer construction separated from each other by insulated coils. Basically this is a configuration shown in the German patent application 37 43 822. Such an arrangement reduces moreover eddy current losses. Another realization is to be seen in the utilization in 10 mm wide copper flat strip with a thickness of about 0.2 mm. This configuration is tuned to a penetration depth for a particular pulse duration under consideration of the mechanical stability of the membrane. The thickness of the insulation is simply determined by the high voltage strength that is required by the circumstances. A particular electrically insulation is known under the name of Kapton and can be used particularly for obtaining the desired insulated strength in the direction of winding which is the longitudinal direction. It should be at least 3 times as wide as the copper strips. The membrane can be shrunk and onto the coil so as to avoid the formation of any gap. Shrinking may e.g. obtain through expansion by heating slipping the expanded coil onto a carrier and cooling to obtain the contraction of the membrane onto the coil.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in conjunction with the accompanying drawings in which:

FIG. 4 illustrates the geometry of the source of FIG. 2 with a cylindrical arrangement and symmetry with a relatively large apertures.

FIGS. 5*a* and 5*b* illustrate respectively two foils to be used in conjunction with an electromagnetic shockwave generator; and FIGS. 6*a* and 6*b* are respectively cross-sections through foils or strips shown in FIGS. 5*a* and 5*b*.

Proceeding now to the detailed description of the drawings, FIG. 1 illustrates the body B of a patient in somewhat schematical cross sectional representation and as it is placed in relation to and adjacent to the shockwave source S. The source is comprised of a ring shaped oscillator and generator proper GR and being physically combined with a reflector R. The overall configuration of the generator GR is that of an annulus but it is specifically of a ring configuration.

The internal, axial face D of that ring GR facing in axial direction towards the reflector R is provided with individual piezoelements E or it may be configured as electromagnetic coil. The elements E or the coil radiate ultrasonic energy basically along i.e. parallel to the axis A and to the left and towards the reflector R. Axis A is the central axis of the paraboloid of the reflector R, and the central axis of ring GR. The beam is actually a parallel hollow beam intercepted by the reflector R that focuses the radiation to the focal point F. The focal point F is situated on the axis A owing to the overall symmetry of the arrangement. The body of reflector R has a cylindrical extension RE and is filled with a liquid and there is a membrane Mb which flexibly closes the interior of that liquid filled space and couples the device acoustically to the body B of the patient. There may be coupling cushions interposed as they are known otherwise.

Figure 1:
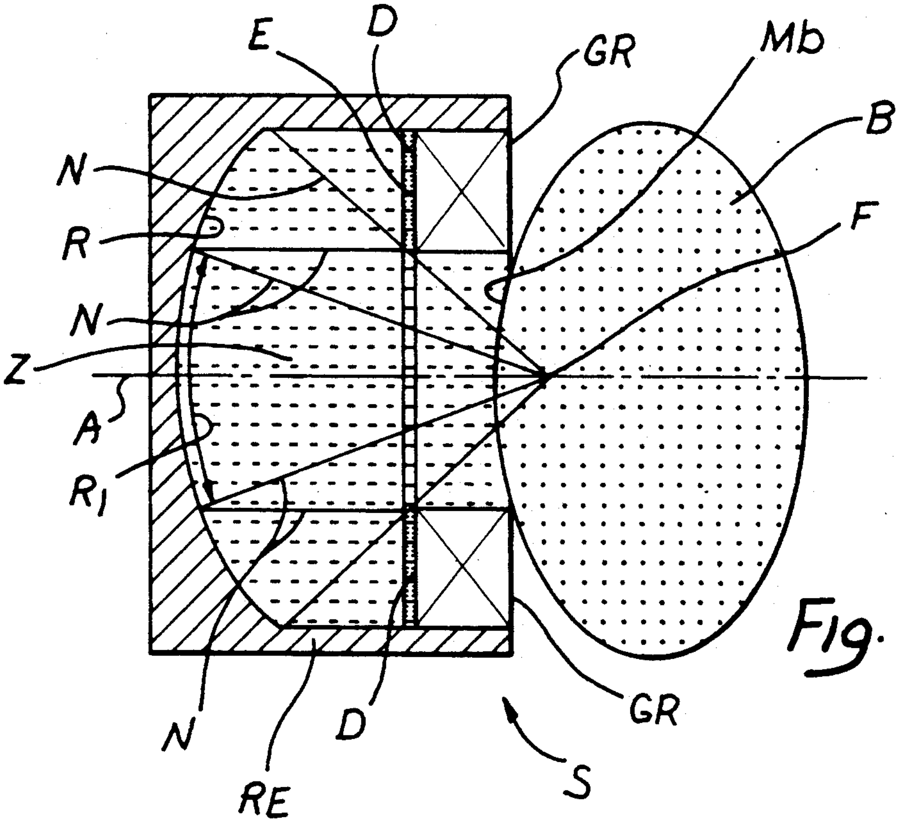
FIGS. 1 and 2 illustrate two cross sections through different configurations for an ultrasonic source and shockwave generator constructed in accordance with the preferred embodiment of the present invention for practicing a best mode configuration. The differences in design are provided to accommodate different operating conditions.

In addition FIG. 1 shows a number of radiation beams N that depict the reflection of individual, elemental beams of radiation, emerging from the generator GR and as they are reflected to converge on the focal point F. Of course the individual beams are produced by the individual elements E. It is of critical, importance for the efficiency of the system that the axis-parallel initial shockwaves are intercepted for reflection only once.

It can readily be seen that in this case the aperture of the ring configuration GR determines the amount of focused energy. On the other hand, the area or zone Z of conical configuration is essentially wavefree and the portion R1 of the reflection surface is actually not needed as a reflecting surface. Here then one can place an ultrasonic locating device and source that directs an imaging search and locating beam through the aperture of the ring so as to find the concrement in body B in the first place.

Figure 2:
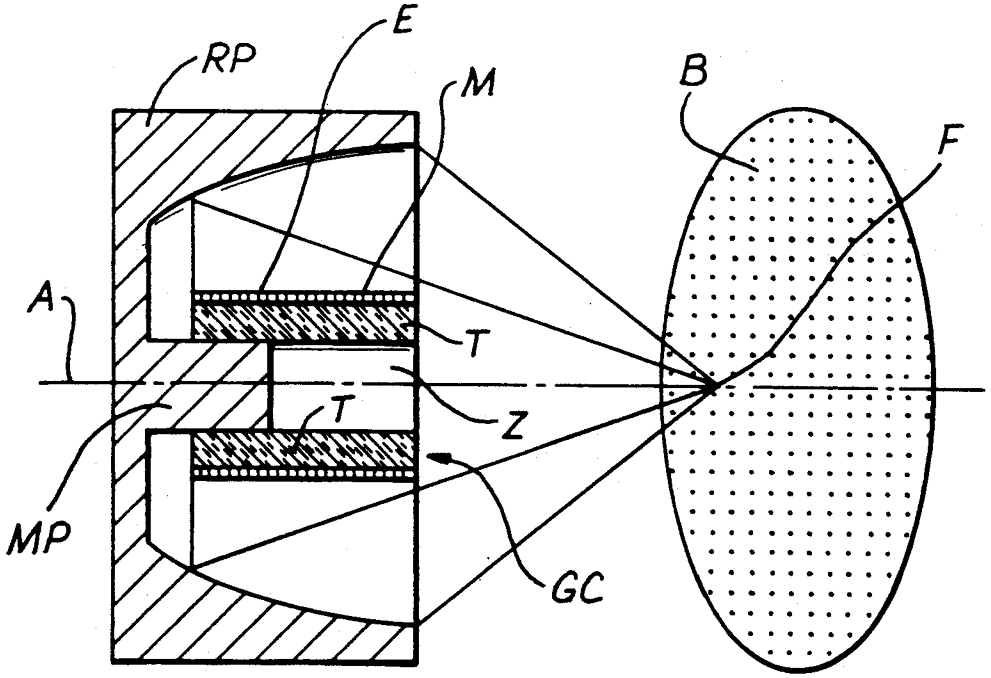

FIGS. 2 (and 4) illustrate another version where the shockwave generating source is of a cylindrical configuration GC having radiating elements E, now on the outer cylindrical surface of a carrier tube T. That tube T in turn sits on a mounting pin MP which extends coaxially (axis A) from the reflection body.

The elements E radiate in radial outer direction. The radial beams are intercepted by parabolic reflector RP which focuses whatever it intercepts on the focal point F of the parabola. The focal point, of course, is again placed to be in a concrement of the body B of the patient. For reasons of simplicity the filling with water and physical closure of the space is omitted also not shown are cushions which may be interposed by the device RP and the body B of the patient. Also here, there is but one reflection of the shockwaves by the reflector.

Figure 3:
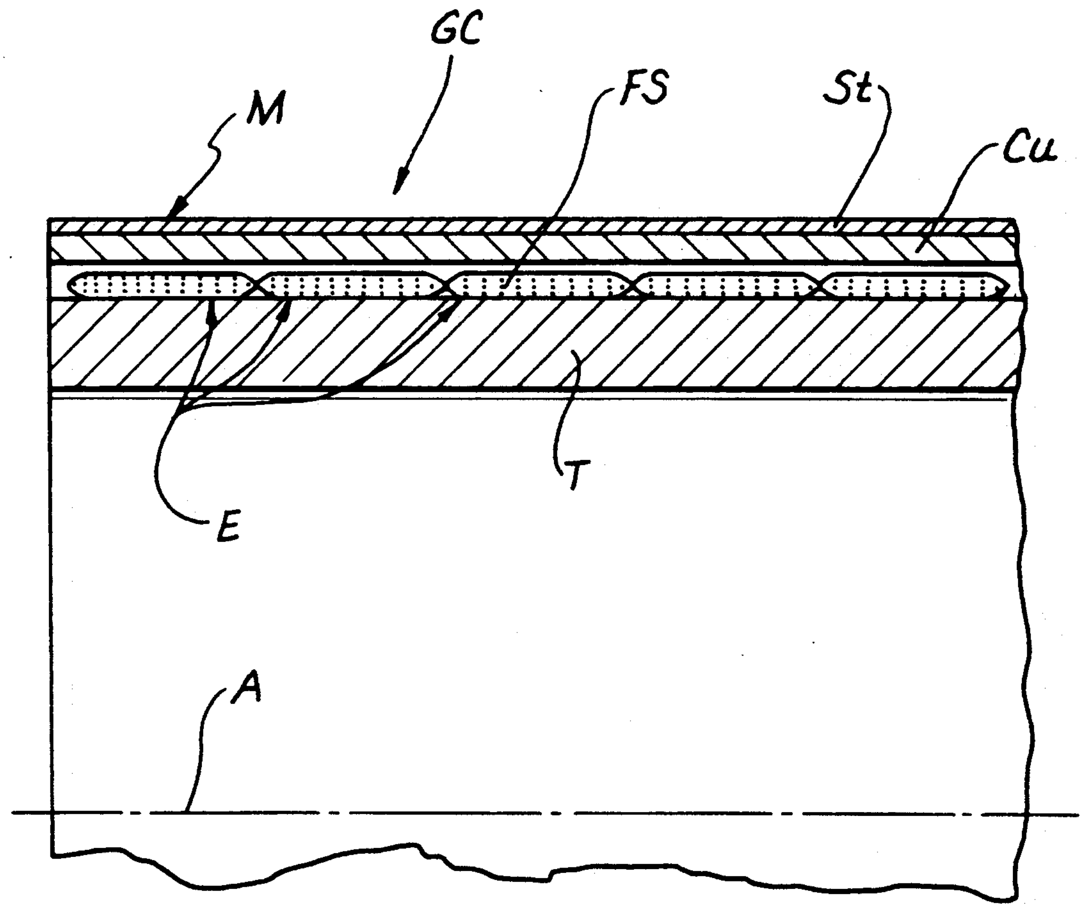
FIG. 3 shows a generator that is included in the source in FIG. 2.

FIG. 3 illustrates in greater detail the shockwave source used in the equipment and lithotripter of FIG. 2. Here the wave generator can be made of a ceramic or a glass like carrier T around which is wound a flat coil FS. The coil may be arranged in the form of copper wire but alternatively a copper coated carrier may be used. The insulative carrier may be of the Kapton variety. Part of the copper has been etched away to obtain a single flat coil like copper layer. Alternatively this arrangement has been made first and wound on top of the cylinder T. This carrier T with the flat coil FS is surrounded by a cylindrical jacket being a membrane of coaxial configuration in relation to the coil and the membrane T. The cylindrical membrane M in this case is comprised of a copper layer CU with a stainless steel layer St.

Insulation, not shown in FIG. 3, and provided between coil FS and membrane M may be established by a separate Kapton layer and through appropriate winding technique the copper coated foil may provide by and in itself this insulating function shown and demonstrated with reference to FIGS. 5*a*, and 5*b*; and 6*a,b*. The gap between insulation of the coil FS and the membrane M should be made small as possible since ideally it should be zero for reasons of dynamics.

FIG. 5*a* and FIG. 5*b* illustrate respectively top views of two examples for Kapton foils KA which in each instance carry a strip of copper Cu. The Kapton foil KA shown in FIG. 5*a* has a copper strip Cu placed in the middle while FIG. 5*b* shows a copper strip Cu on just one side of the respective Kapton layer KA. FIGS. 6*a* and 6*b* show that in each instance a portion of the copper has been etched away thus exposing the Kapton KA underneath, on one side only in the version of FIGS. 5*b* and 6*b*, and to both sides of the copper strip configuration shown in FIGS. 5*a* and 6*a*. Upon helically winding the foil onto a carrier tube, a cylindrical layer is provided so that a copper strip winding is situated next to another one. This way one obtains indeed a flat coil. The Kapton layers overlay in that e.g. each left side Kapton layer is situated on top of the previously wound copper layer Cu and serve as insulation therefrom. In the case of winding a coil from the configurations of FIGS. 5*b* and 6*b* two insulating layer portions in fact overlap.

FIG. 4 illustrates somewhat schematically the cylindrical shockwave generator GC with a radially or effective outer source radiating cylindrical radially expanding shockwaves towards a parabolic reflector R. Basically this is a geometric simplification of the configuration shown in FIG. 2. However one can take the various physical dimensions in relation to each other including particularly diameter and length dimensions and angles. FIG. 4 is in effect drawn to scale realizing a length L of 13 cm for the coil, a coil diameter D of 6 cm and focal length of 15 cm for an aperture of about 42.4 degrees. The maximum diameter of the paraboloid is 27.4 cm. The radiating source thereby corresponds to a planar electromagnetic shockwave source having almost 18 cm diameter. Owing to the finite radius of the cylindrical source there is a minimal aperture angle that however is not obtained through shading of the source. Axially extending the cylinder on the other hand permits enlargement of the surface whereby the parabola diameter of course increases in a proportional fashion. Searching for and locating a concrement is in that case possible through the central opening of the source which is given by the open interior of carrier tube T.

The radially radiated waves will be redirected by the parabolic reflector RP to converge upon the focal point F being situated on the central axis A of the system. The relationship between opening angle $\phi$ and distance H between the linear source and the focus F is given here by $H=Px \cos \phi(1+\sin \phi)$ whereby P is the parabola parameter given by the equation $y^2=2$ px. The focal point is then located at $x=p/2$. There is a corresponding relationship to tangents $\phi$ being given by the relationship $(p/H-H/p)/2$. This geometry has the advantage that one obtains a small compact areal source of high aperture that focuses very well. The pressure amplitude of high aperture which focuses very well. The pressure amplitude follows from a law for a cylindrical source and is increased in a central area or range as follows: f is proportional to $[\sin \phi(1+\sin \phi)]^{-0.5}$.

The invention is not limited to the embodiments described above but all changes and modifications thereof, not constituting departures from the spirit and scope of the invention, are intended to be included.

We claim:

1. Device for producing shockwaves comprising
a cylindrically shaped wave generator having (i) a carrier tube with a cylindrical surface and a central axis and (ii) further having a coil on said cylindrical surface of the carrier tube, said coil being areally configured on said cylindrical surface for radiating shockwaves in radially outward directions with respect to said axis of said cylindrical surface; and
a parabolically shaped reflector having an axis that coincides with said central axis of the carrier tube, said reflector circumscribing the generator so that said outwardly radiated shockwaves from the generator are reflected by the reflector towards a focal point on said central axis.

2. Device as in claim 1, said cylindrical surface facing outwardly, and the coil including at least one radiating element for radiating shockwaves from said cylindrical surface, radiating in said radially outward directions toward the parabolically shaped reflector.

3. Device as in claim 1, wherein said coil is an electromagnetic coil.

4. Device as in claim 3, the generator including a cylindrical membrane around the coil, the membrane being provided for being acted upon by said coil for deflecting the membrane, the membrane being coaxial with the axis of the parabolically shaped reflector.

5. Device for producing shockwaves comprising:
a cylindrically shaped generator having an axis and a hollow cylindrical carrier having a cylindrical outer surface and being coaxial with said axis, further having means on said cylindrical outer surface of the carrier, for radiating shockwaves in radially outward directions; and
parabolically shaped reflector circumscribing the generator and its axis and facing the cylindrical outer surface of the carrier of the generator, for directly reflecting the shockwaves radiating radially outwardly from the generator toward a particular point on said axis, said particular point thus being a focal point.

6. Source and device as in claim 5, the means for radiating being a plurality of piezoelectric elements.

7. Device as in claim 5, the means on said cylindrical surface for radiating including a cylindrical coil and a cylindrical membrane, the coil being mounted on said carrier, the membrane being mounted on said coil.

8. Device as in claim 7, the coil including a copper layer, and a stainless steel layer on said copper layer.

9. Device as in claim 7, the coil having been thermally shrunken onto said carrier.

* * * * *